United States Patent [19]
Walter et al.

[11] Patent Number: 6,083,880
[45] Date of Patent: Jul. 4, 2000

[54] SACCHARINE-5-CARBONYL-CYCLOHEXANE-1, 3, 5-TRIONE DERIVATIVES, THEIR PREPARATION AND THEIR USE AS HERBICIDES

[75] Inventors: Helmut Walter, Obrigheim; Peter Plath, Frankenthal; Uwe Kardorff, Mannheim; Matthias Witschel, Ludwigshafen; Regina Luise Hill, Speyer; Wolfgang von Deyn, Neustadt; Stefan Engel, Idstein; Martina Otten, Ludwigshafen; Ulf Misslitz, Neustadt; Karl-Otto Westphalen, Speyer, all of Germany

[73] Assignee: BASF Aktiengesellschaft, Ludwigshafen, Germany

[21] Appl. No.: 09/380,381
[22] PCT Filed: Feb. 18, 1998
[86] PCT No.: PCT/EP98/00926
  § 371 Date: Sep. 1, 1999
  § 102(e) Date: Sep. 1, 1999
[87] PCT Pub. No.: WO98/40366
  PCT Pub. Date: Sep. 17, 1998

[30] Foreign Application Priority Data

Mar. 10, 1997 [DE] Germany ............... 197 09 697

[51] Int. Cl.⁷ .................... A01N 43/80; C07D 275/06
[52] U.S. Cl. ........................... 504/269; 548/210
[58] Field of Search ............... 548/210; 504/269

[56] References Cited

U.S. PATENT DOCUMENTS 5,744,425  4/1998  Plath et al. ............... 504/269

FOREIGN PATENT DOCUMENTS

| | | |
|---|---|---|
| 2197120 | 2/1996 | Canada. |
| 252 298 | 1/1988 | European Pat. Off.. |
| 283 261 | 9/1988 | European Pat. Off.. |
| 594 257 | 4/1994 | European Pat. Off.. |
| 97/08164 | 3/1997 | WIPO. |

OTHER PUBLICATIONS

JP 7200419—Abstract, 1972.
JP 7335457—Abstract, 1974.
Spitzer, Monatshefter der Chem. 11, 104 (1890).
Riedl et al., Liebigs Ann. Chem. 585, 209 (1954).
Murin et al., Chem. Ber. 92, 2033 (1959).

*Primary Examiner*—Laura L. Stockton
*Attorney, Agent, or Firm*—Keil & Weinkauf

[57] ABSTRACT

Saccharin-5-carbonylcyclohexane-1,3,5-trione derivatives of the formula I

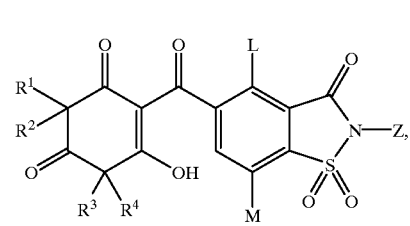

where:

L is $C_1$–$C_3$-alkyl or $C_1$–$C_3$-alkoxy;

Z is $C_1$–$C_4$-alkyl, $C_3$–$C_8$-cycloalkyl, $C_3$–$C_6$-alkenyl, $C_3$–$C_5$-alkynyl, benzyl or phenyl, the phenyl rings in each case being unsubstituted or mono- or polysubstituted by $C_1$–$C_4$-alkyl, $C_1$–$C_3$-alkoxy or halogen;

M is hydrogen, $C_1$–$C_3$-alkyl, $C_1$–$C_3$-alkoxy, fluorine, chlorine, cyano, nitro or trifluoromethyl;

$R^1$, $R^2$, $R^3$, $R^4$ are each $C_1$–$C_4$-alkyl;

and agriculturally useful salts of compound I.

8 Claims, No Drawings

SACCHARINE-5-CARBONYL-CYCLOHEXANE-1, 3, 5-TRIONE DERIVATIVES, THEIR PREPARATION AND THEIR USE AS HERBICIDES

This application is a 371 of PCT/EP98/00926 filed Feb. 18, 1998.

The present invention relates to saccharin-5-carbonylcyclohexane-1,3,5-trione derivatives of the formula I

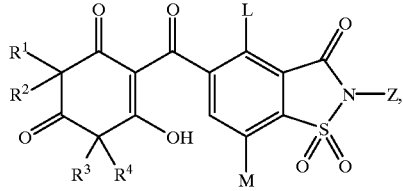

where:

L is $C_1-C_3$-alkyl or $C_1-C_3$-alkoxy;

Z is $C_1-C_4$-alkyl, $C_3-C_8$-cycloalkyl, $C_3-C_6$-alkenyl, $C_3-C_5$-alkynyl, benzyl or phenyl, the phenyl rings in each case being unsubstituted or mono- or polysubstituted by $C_1-C_4$-alkyl, $C_1-C_3$-alkoxy or halogen;

M is hydrogen, $C_1-C_3$-alkyl, $C_1-C_3$-alkoxy, fluorine, chlorine, cyano, nitro or trifluoromethyl;

$R^1$, $R^2$, $R^3$, $R^4$ are each $C_1-C_4$-alkyl;

and agriculturally useful salts of compound I.

The invention further relates to herbicidal compositions comprising compounds I and to methods for controlling undesirable vegetation using the saccharin derivatives I.

Herbicidally active saccharincarbonylcyclohexanedione derivatives are known from WO 96/05182.

EP-A 252 298 describes herbicidal benzoyl-1,3,5-cyclohexanetriones, but these compounds do not have a saccharin structure.

It is further known to use saccharin derivatives as fungicides, for example from JP Publication 72/00419 and 73/35457, and in pharmacy, for example from EP-A 594 257.

However, the herbicidal properties of these prior art compounds and their tolerance by crop plants are not entirely satisfactory.

It is an object of the present invention to provide novel saccharin derivatives having improved properties.

We have found that this object is achieved by the saccharin-5-carbonylcyclohexane-1,3,5-trione derivatives of the general formula I defined at the outset.

Compounds of the formula I are obtained according to scheme 1 by acylating cyclohexane-1,3,5-triones of the formula II with a saccharin-5-carbonyl chloride of the formula III and rearranging the resulting enol ester of the formula IV in the presence of a catalyst to give the active compound of the formula I.

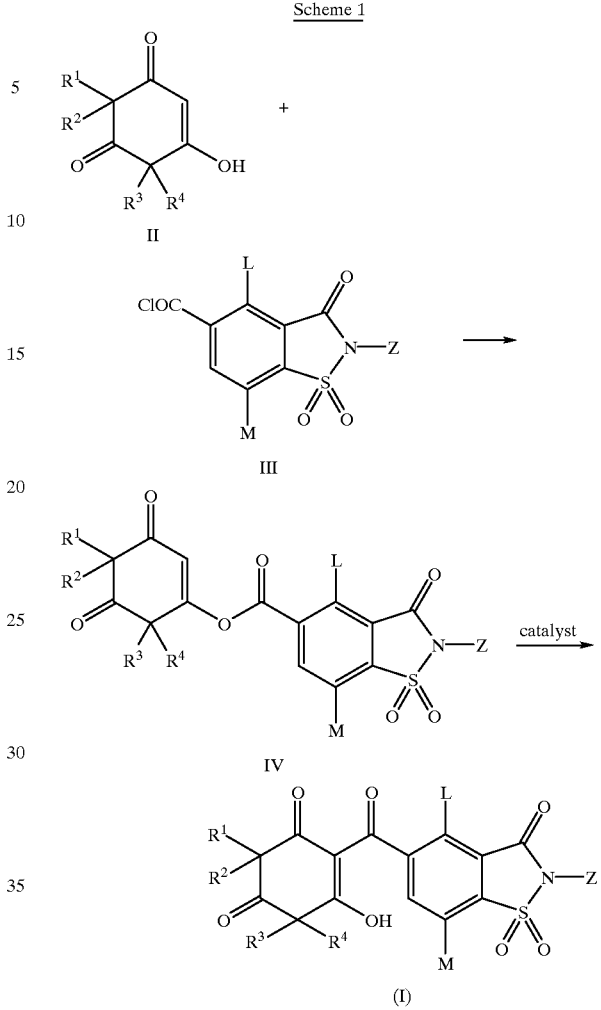

In scheme 1 above, the substituents $R^1$ to $R^4$, L, M and Z are each as defined at the outset.

The first step of the reaction sequence in scheme 1 is carried out by adding the acyl chloride III to a solution or suspension of the cyclohexane-1,3,5-trione II in the presence of an auxiliary base. The reactants and the auxiliary base are preferably employed in equimolar amounts, but a slight excess of from 1.2 to 1.5 mole equivalents of the auxiliary base may be advantageous. Suitable solvents are methylene chloride, tetrahydrofuran, ethyl acetate, toluene or, preferably, acetonitrile. Suitable auxiliary bases are alkali metal carbonates, pyridine or tertiary alkylamines, preferably triethylamine. During the addition of the acyl chloride, the reaction mixture is preferably cooled to from 0 to 10° C., and thereafter, the mixture is stirred at from 20 to 70° C., in particular from 25 to 40° C., until the reaction has ended.

The enol ester IV can be isolated prior to the rearrangement, but the reaction is preferably carried out by admixing the reaction mixture with from two to four, preferably 2.5, equivalents of triethylamine and subsequently, at 25° C., adding from 2 to 10, in particular 3, mol % of a cyano compound such as acetone cyanohydrin or preferably trimethylsilyl cyanide and then stirring the reaction mixture at from 20 to 40° C., preferably at 25° C., until no more enol ester IV is present. Examples of the cyanide-catalyzed rearrangement of enol esters of cyclohexane-1,3,5-triones are given in EP-A 252 298.

Work-up is carried out by acidifying the reaction mixture with 5% strength hydrochloric acid or sulfuric acid and subsequent extraction with a solvent such as ethyl acetate or methylene chloride. The extract is dried over sodium sulfate or magnesium sulfate, the solvent is distilled off under reduced pressure and the crude product is, if required, purified. The reaction product is purified for example by chromatography (silica gel, cyclohexane/ethyl acetate) or recrystallization (methanol/water or glacial acetic acid/water). A further purification method is the extraction of a solution of the crude product in ethyl acetate with an aqueous alkali metal carbonate solution, in which the end product passes over into the aqueous phase. Acidification of the aqueous solution and reextraction affords, after drying and removal of the solvent, the pure end product.

The cyclohexane-1,3,5-triones of the formula II used as starting material are known and can be prepared in a conventional manner [cf. Spitzer, Monatshefte der Chemie 11 (1890), 104, Riedl et al., Liebigs Ann. Chem. 585 (1954), 209 and Murin et al. Chem. Ber. 92 (1959), 2033]. EP-A 283 152 describes a process for preparing the particularly preferred 2,2,4,4-tetramethylcyclohexane-1,3,5-trione.

The acyl chlorides of the formula III used as starting material are also known. They are obtained by reacting an appropriately substituted saccharin-5-carboxylic acid with thionyl chloride. The synthesis of substituted saccharin-5-carboxylic acids is described, for example, in DE 44 27 996.

In the definition of the compounds I given at the outset, collective terms were used which, in a general way, represent the following groups:

Alkyl: straight-chain or branched alkyl groups having from 1 to 4 carbon atoms, for example $C_1$–$C_4$-alkyl such as methyl, ethyl, propyl, 1-methylethyl, butyl, 1-methylpropyl, 2-methylpropyl and 1,1-dimethylethyl;

Alkoxy: straight-chain or branched alkyl groups having from 1 to 3 carbon atoms as mentioned above which are linked to the skeleton via an oxygen atom (—O—), for example $C_1$–$C_3$-alkoxy such as methyloxy, ethyloxy, propyloxy and 1-methylethyloxy;

Cycloalkyl: monocyclic alkyl groups having from 3 to 8 carbon ring members, for example cyclopropyl, cyclobutyl, cyclopentyl, cyclohexyl, cycloheptyl and cyclooctyl;

Alkenyl: straight-chain or branched alkenyl groups having from 2 to 6 carbon atoms and a double bond in any desired position, for example $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having from 3 to 5 carbon atoms and a triple bond in any desired position, for example $C_3$–$C_5$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl and 1-ethyl-2-propynyl;

Halogen: fluorine, chlorine, bromine and iodine.

With respect to their intended use as herbicides, preference is given to saccharin-5-carbonylcyclohexane-1,3,5-trione derivatives of the formula I where the substituents have the following meaning:

L is methyl, ethyl, methoxy or ethoxy; furthermore preferably methyl and methoxy and particularly preferably methyl;

Z is $C_1$–$C_4$-alkyl, $C_3$–$C_8$-cycloalkyl, $C_3$–$C_6$-alkenyl, $C_3$–$C_5$-alkynyl, benzyl and phenyl; furthermore preferably methyl, ethyl, i-propyl, i-butyl, t-butyl, cyclopropyl; cyclohexyl, allyl, propargyl, phenyl and benzyl; particularly preferably methyl, ethyl and phenyl and very particularly preferably methyl;

M is hydrogen, methyl, ethyl, methoxy, ethoxy, fluorine, chlorine, cyano, nitro and trifluoromethyl; furthermore preferably hydrogen, methyl, ethyl, methoxy and chlorine; particularly preferably hydrogen, methyl and chlorine;

$R^1$, $R^2$, $R^3$, $R^4$ are each methyl, ethyl, n-propyl and n-butyl; furthermore preferably methyl and ethyl; particularly preferably methyl.

Preference is also given to combinations of the above-mentioned preferred substituents.

Very particular preference is given to saccharin derivatives of the formula I where L and $R^1$ to $R^4$ are each methyl, Z is methyl and M is hydrogen, methyl or chlorine.

The compounds I may be present in the form of their agriculturally useful salts, the kind of salt generally not being important. Generally, the salts of those bases are suitable where the herbicidal activity of I is not adversely affected.

Suitable basic salts are in particular those of the alkali metals, preferably the sodium and potassium salts, of the alkaline earth metals, preferably the calcium, magnesium and barium salts, of the transition metals, preferably manganese, copper, zinc and iron salts, and ammonium salts, which may carry from one to three $C_1$–$C_4$-alkyl, hydroxy-$C_1$–$C_4$-alkyl substituents and/or one phenyl or benzyl substituent, preferably diisopropylammonium, tetramethylammonium, tetrabutylammonium, trimethylbenzylammonium, and trimethyl-(2-hydroxyethyl) ammonium salts, phosphonium salts, sulfonium salts, preferably tri-($C_1$–$C_4$-)alkylsulfonium salts, and sulfoxonium salts, preferably tri-($C_1$–$C_4$-)alkylsulfoxonium salts.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and weed grasses in crops such as wheat, rice, maize, soya and cotton without causing any significant damage to the crop plants. This effect is mainly observed at low rates of application.

Depending on the application method in question, the compounds I, or compositions comprising them, can additionally be employed in a further number of crop plants for eliminating undesirable plants. Examples of suitable crops are the following: *Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N.rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays*.

In addition, the compounds I may also be used in crops which tolerate the action of herbicides owing to breeding, including genetically engineered breeding.

The active compounds or the herbicidal compositions can be applied pre- or post-emergence. If the active compounds are less well tolerated by certain crop plants, application techniques may be used in which the herbicidal compositions are spray-dispensed, with the aid of spraying equipment, in such a way that they ideally do not come into contact with the leaves of the sensitive crop plants, while the active ingredients reach the leaves of undesirable plants growing underneath, or the bare soil surface (post-directed, lay-by).

The compounds I, or the herbicidal compositions comprising them, can be applied, for example, in the form of ready-to-spray aqueous solutions, powders, suspensions, including highly-concentrated aqueous, oily or other suspensions or dispersions, emulsions, oil dispersions, pastes, dusts, materials for spreading, or granules, by spraying, atomizing, dusting, spreading or watering. The application forms depend on the intended purpose; in any case, they should guarantee very fine dispersion of the active ingredients according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the compounds I, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active compounds together with a solid carrier.

Granules, eg. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise approximately from 0.001 to 98% by weight, preferably 0.01 to 95% by weight of at least one active compound. The active compounds are employed in a purity of from 90% to 100%, preferably 95% to 100% (according to NMR spectrum). The examples which follow illustrate the formulation of the compounds I according to the invention:

I 20 parts by weight of the compound No. 1.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely dispersing it therein gives an aqueous dispersion which comprises 0.02% by weight of the active compound.

II 20 parts by weight of the compound No. 1.1 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely dispersing it therein gives an aqueous dispersion which comprises 0.02% by weight of the active compound.

III 20 parts by weight of the active compound No. 1.1 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely dispersing it therein gives an aqueous dispersion which comprises 0.02% by weight of the active compound.

IV 20 parts by weight of the active compound No. 1.1 are mixed thoroughly with 3 parts by weight of the sodium salt of diisobutylnaphthalenesulfonic acid, 17 parts by weight of the sodium salt of a lignosulfonic acid from a sulfite waste liquor and 60 parts by weight of pulverulent silica gel, and the mixture is ground in a hammer mill. Finely dispersing the mixture in 20,000 parts by weight of water gives a spray mixture which comprises 0.1% by weight of the active compound.

V 3 parts by weight of the active compound No. 1.1 are mixed with 97 parts by weight of finely divided kaolin. This gives a dust which comprises 3% by weight of the active compound.

VI 20 parts by weight of the active compound No. 1.1 are mixed intimately with 2 parts by weight of calcium dodecylbenzenesulfonate, 8 parts by weight of fatty alcohol polyglycol ether, 2 parts by weight of sodium salt of a phenol/urea/formaldehyde condensate and 68 parts by weight of a paraffinic mineral oil. This gives a stable oily dispersion.

VII 1 part by weight of the compound No. 1.1 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound No. 1.1 is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the spectrum of action and to achieve synergistic effects, the compounds I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and their derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-CF3-phenyl derivatives, carbamates, quinolinecarboxylic acid and its derivatives, chloroacetanilide, cyclohexane-1,3-dione derivatives, diazines, dichloropropionic acid and its derivatives, dihydrobenzenefurans, dihydrofuran-3-ones, dinitroanilines, dinitrophenols, diphenyl ether, dipyridyls, halocarboxylic acid and its derivatives, urea, 3-phenyluracils, imidazoles, imidazolinones, N-phenyl-3,4, 5,6-tetrahydrophthalimides, oxadiazoles, oxiranes, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The rates of application of active compound are from 0.001 to 3.0, preferably 0.01 to 1.0 kg/ha of active substance (a.s.), depending on the control target, the season, the target plants and the growth stage

PREPARATION EXAMPLES

Active compound from 2,2,4,4-tetramethylcyclohexane-1,3,5-trione and 2,4-dimethylsaccharin-5-acyl chloride (No. 1 in Table 1)

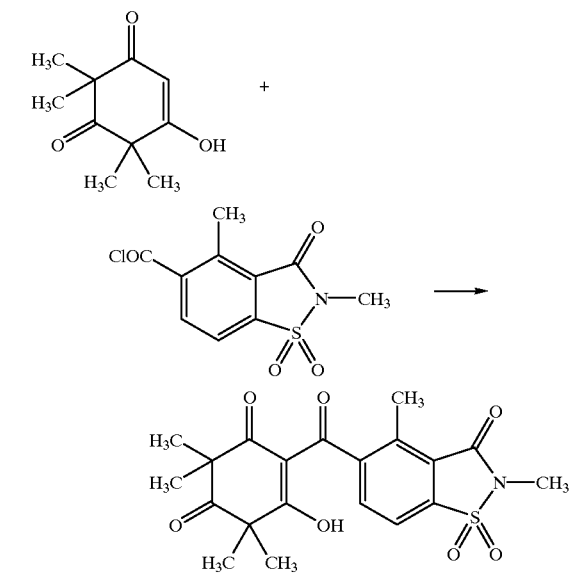

0.91g (0.005 mol) of 2,2,4,4-tetramethylcyclohexane-1,3, 5-trione are suspended in 25 ml of acetonitrile, and 0.6 g (0.005 mol) of triethylamine are added. Subsequently, 1.37 g (0.005 mol) of 2,4-dimethylsaccharin-5-acyl chloride are added as one portion at 25° C., and the reaction mixture is stirred without cooling for 4 hours. Another 1.2 g (0.012 mol) of triethylamine and then 10 drops of trimethylsilyl cyanide are added and the mixture is stirred at 25° C. for 16 hours. Completion of the rearrangement of the enol ester is achieved by heating the mixture to 40° C. for 2 hours.

For work-up, the reaction mixture is evaporated to dryness using a rotary evaporator and the residue is admixed with 30 ml of water, acidified to pH 1 with 5% strength HCl and extracted three times with ethyl acetate. The extract is dried over sodium sulfate and the solvent is removed using the rotary evaporator, affording 2.1 g of a solid. Recrystallization from a mixture of 5 parts of glacial acetic acid and 1 part of water yields 0.9 g (43% of theory) of a white solid of m.p. 210° C.

The following compounds of Table 1 can be obtained in the same manner:

TABLE 1

(I)

[Structure: Compound of formula (I) with substituents R¹, R², R³, R⁴ on cyclohexanedione ring connected via carbonyl to benzisothiazolone ring with L, M, Z substituents]

| No. | R¹, R², R³, R⁴ | L | M | Z | mp ° C. |
|---|---|---|---|---|---|
| 1.1 | $CH_3$ | $CH_3$ | H | $CH_3$ | 210 |
| 1.2 | $CH_3$ | $CH_3$ | $CH_3$ | $CH_3$ | 193 |
| 1.3 | $CH_3$ | $CH_3$ | $CH_3$ | $i-C_3H_7$ | |
| 1.4 | $CH_3$ | $CH_3$ | F | $i-C_4H_9$ | |
| 1.5 | $CH_3$ | $CH_3$ | Cl | $t-C_4H_9$ | |
| 1.6 | $CH_3$ | $CH_3$ | CN | cyclopropyl | |
| 1.7 | $CH_3$ | $CH_3$ | $OCH_3$ | cyclohexyl | |
| 1.8 | $CH_3$ | $CH_3$ | $NO_2$ | $CH_3$ | |
| 1.9 | $CH_3$ | $CH_3$ | $CF_3$ | $CH_3$ | |
| 1.10 | $CH_3$ | $CH_3$ | $C_2H_5$ | $CH_3$ | |
| 1.11 | $CH_3$ | $CH_3$ | H | allyl | |
| 1.12 | $CH_3$ | $CH_3$ | H | propargyl | |
| 1.13 | $CH_3$ | $CH_3$ | H | phenyl | |
| 1.14 | $CH_3$ | $CH_3$ | H | benzyl | |
| 1.15 | $C_2H_5$ | $CH_3$ | H | $CH_3$ | |
| 1.16 | $n-C_3H_7$ | $CH_3$ | H | $CH_3$ | |
| 1.17 | $n-C_4H_9$ | $CH_3$ | H | $CH_3$ | |
| 1.18 | $CH_3$ | $OCH_3$ | H | $C_2H_5$ | |
| 1.19 | $CH_3$ | $OC_2H_5$ | H | $CH_3$ | |
| 1.20 | $CH_3$ | $CH_3$ | Cl | phenyl | |

USE EXAMPLES

The herbicidal activity of the compounds of the formula I was demonstrated by greenhouse experiments:

The culture containers used were plastic pots containing loamy soil with approximately 3.0% of humus as the substrate. The seeds of the test plants were sown separately for each species.

For the pre-emergence treatment, the active compounds, which had been suspended or emulsified in water, were applied directly after sowing by means of finely dispersing nozzles. The containers were irrigated gently to promote germination and growth and subsequently covered with translucent plastic hoods until the plants had rooted. This cover causes uniform germination of the test plants, unless this was adversely affected by the active ingredients. The application rate for the pre-emergence treatment was 0.5 or 0.25 kg/ha of a.s.

For the post-emergence treatment, the test plants were first grown to a plant height of 3 to 15 cm, depending on the plant habit, and only then treated with the active compounds which had been suspended or emulsified in water. The test plants for this purpose were either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

TABLE 2

| Scientific name | Common name | Abbreviation |
|---|---|---|
| Gossypium hirsutum | cotton | GOSHI |
| Amaranthus retroflexus | redroot pigweed | AMARE |
| Digitaria sanguinalis | fingergrass | DIGSA |
| Echinochloa crus-galli | barnyardgrass | ECHCG |
| Setaria faberii | giant foxtail | SETFA |
| Setaria viridis | green foxtail | SETVI |

Selective herbicidal activity when applied pre-emergence (greenhouse)

TABLE 3

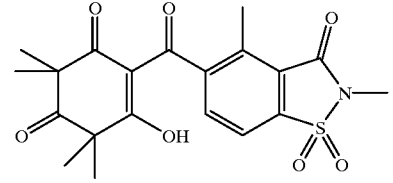

| Ex. No. | 1.1 | |
|---|---|---|
| Application rate (kg/ha of a.s.) Test plants | 0.5 | 0.25 |
| GOSHI | 0 | 0 |
| AMARE | 98 | 98 |
| ECHCG | 98 | 98 |
| SETFA | 100 | 100 |

Selective herbicidal activity when applied pre-emergence (greenhouse)

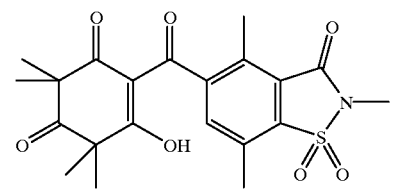

| Ex. No. | 1.2 | |
|---|---|---|
| Application rate (kg/ha of a.s.) Test plants | 0.5 | 0.25 |
| GOSHI | 10 | 10 |
| DIGSA | 100 | 100 |
| ECHCG | 98 | 98 |
| SETVI | 100 | 95 |

We claim:

1. A saccharin-5-carbonylcyclohexane-1,3,5-trione derivative of the formula I

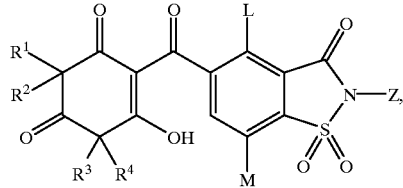

(I)

where
- L is $C_1$–$C_3$-alkyl;
- Z is $C_1$–$C_4$-alkyl;
- M is hydrogen, $C_1$–$C_3$-alkyl;
- $R^1$, $R^2$, $R^3$, $R^4$ are each $C_1$–$C_4$-alkyl;
- or an agriculturally useful salt of formula I.

2. A saccharin derivative of the formula I as claimed in claim 1, where L is methyl or ethyl.

3. A saccharin derivative of the formula I as claimed in claim 1, where Z is methyl, ethyl, i-propyl, i-butyl or t-butyl.

4. A saccharin derivative of the formula I as claimed in claim 1, where M is hydrogen, methyl or ethyl.

5. A saccharin derivative of the formula I as claimed in claim 1, where $R^1$ to $R^4$ are each methyl, ethyl, n-propyl or n-butyl.

6. A saccharin derivative of the formula I as claimed in claim 1, where $R^1$ to $R^4$ are each methyl or ethyl.

7. A saccharin derivative of the formula I as claimed in claim 1, where L and $R^1$ to $R^4$ are each methyl, Z is methyl and M is hydrogen or methyl.

8. A herbicidal composition comprising at least one saccharin derivative of the formula I as claimed in claim 1 and customary inert additives.

* * * * *